US009889117B2

(12) United States Patent
Lin et al.

(10) Patent No.: US 9,889,117 B2
(45) Date of Patent: Feb. 13, 2018

(54) METHOD FOR TREATING AND/OR DELAYING THE DEGENERATION OF PURKINJE CELLS

(71) Applicant: EVERFRONT BIOTECH INC., New Taipei (TW)

(72) Inventors: Shinn-Zong Lin, New Taipei (TW); Horng-Jyh Harn, New Taipei (TW); Tzyy-Wen Chiou, New Taipei (TW); Cheng-Han Wu, New Taipei (TW); Ssu-Yin Yen, New Taipei (TW)

(73) Assignee: EVERFRONT BIOTECH INC., New Taipei (TW)

( * ) Notice: Subject to any disclaimer, the term of this patent is extended or adjusted under 35 U.S.C. 154(b) by 0 days.

(21) Appl. No.: 14/504,180

(22) Filed: Oct. 1, 2014

(65) Prior Publication Data

US 2016/0000751 A1 Jan. 7, 2016

(30) Foreign Application Priority Data

Jul. 2, 2014 (TW) .............................. 103122820 A

(51) Int. Cl.
*A61K 31/365* (2006.01)
(52) U.S. Cl.
CPC ................................. *A61K 31/365* (2013.01)
(58) Field of Classification Search
None
See application file for complete search history.

(56) References Cited

U.S. PATENT DOCUMENTS

| 2006/0051851 A1 | 3/2006 | Kaminaka et al. |
| 2007/0178178 A1 | 8/2007 | Xia |

FOREIGN PATENT DOCUMENTS

| CN | 101184484 A | 5/2008 |
| CN | 101455661 | 6/2009 |
| CN | 101455661 A * | 6/2009 |
| CN | 101455661 A | 6/2009 |
| CN | 101904838 A | 12/2010 |
| EP | 2 992 879 A | 9/2016 |
| JP | 2002-068973 | 3/2002 |
| JP | 2003-089695 | 3/2003 |
| JP | 2011-173866 | 9/2011 |
| JP | 2012-144512 | 8/2012 |
| JP | 2013-234179 | 11/2013 |
| WO | 03/029469 | 4/2003 |
| WO | 2014/026372 A | 2/2014 |

OTHER PUBLICATIONS

Shaner et al. in Pesticide Biotransformation in Plants and Microorganisms (Hall, J. et al.); ACS Symposium Series, American Chemical Society: Washington, DC, 2000.*
Mavroudis et al. in Psychiatria Danubina, 25(3), p. 221-226 (2013).*
Chakraborty et al. in PLoS ONE 6(6):e20799 (2011).*
Farr et al. in Journal of Alzheimer's Disease 28(1):81-92 (2012).*
Morley J.E. in Biogerentology 3:57-60 (2002).*
Goodman and Gilman's The Pharmacological Basis of Therapeutics, Tenth Edition (2001), McGraw Hill, Chapter I, pp. 3-29.*
Brindis et al. in Journal of Natural Products 74, 314-320 (2011).*
Preventing Alzheimer's Disease at www.nia.nih.gov/alzheimers/publication/ preventing-alzheimers-disease/risk-factors-alzheimers-disease (retrieved from the internet on Sep. 21, 2016).*
Cao et al. in ACS Appl. Mater. Interfaces 4, 3773-3778 (2012).*
Pablo et al. in Current Pharmaceutical Design, 17(8), 769-777 (2011) (Abstract).*
Schilling, K. et al., "Electrical Activity in Cerebellar Cultures Determines Purkinje Cell Dendritic Growth Patterns", Neuron, Vo. 7, pp. 891-902, Dec. 1991.
Kuang, X. et al., "Protective effect of Z-ligustilide against amyloid beta-induced neurotoxicity is associated with decreased pro-inflammatory markers in rat brains," Pharmacology, Biochemistry and Behavior, Jun. 2009, vol. 92(4), pp. 635-641.
Fu, R. H. et al., "n-Butylidenephthalide Protects against Dopaminergic Neuron Degeneration and α-Synuclein Accumulation in Caenorhabditis elegans Models of Parkinson's Disease," PLOS One, Jan. 8, 2014, vol. 9(1), pp. 1-14.
Zoghbi, Y. H. et al., "Pathogenic Mechanisms of a Polyglutamine-mediated Neurodegenerative Disease, Spinocerebellar Ataxia Type 1", The Journal of Biological Chemistry, vol. 284 (2009) pp. 7425-7429.
Qian, H., "Ubiquitin/proteasome pathway impairment in neurodegeneration: therapeutic implications", Apoptosis, vol. 15 (2010), pp. 1292-1311.
Xu-Dong, C. et al., "Proliferation and differentiation of neural stem cells and the affection of Angelica sinensis on the same", Sichuan Journal of Anatomy, 2007, vol. 15(2), pp. 18-21.
Yu, W. et al., "Effect of Z-ligustilide on $GABA_A$ receptor in vitro and in vivo", West China Journal of Pharmaceutical Sciences, 2014, vol. 29(2), pp. 152-154.
Bezprozvanny, I. et al "Therapeutic prospects for spinocerebellar ataxia type 2 and 3", Drugs Future, 2009, vol. 34 (12), pp. 1-17.
Kuang, X. et al., "Neuroprotective role of Z-ligustilide against forebrain ischemic injury in ICR mice", Brain Res., 2006, vol. 1102(1), pp. 145-153.
Kuang, X. et al., "Klotho upregulation contributes to the neuroprotection of ligustilide in an Alzheimer's disease mouse model", Neurobiol Aging., 2014, vol. 35(1), pp. 169-178.
Li, P. et al., "Optimization of pressurized liquid extraction for Z-ligustilide, Z-butylidenephthalide and ferulic acid in Angelica sinensis" J Pharm Biomed Anal., 2006, vol. 40(5), pp. 1073-1079. A10353 n-Butylidenephthalide, (E) +(Z), 95%.
Murakami, H., "Utilizationof Optically Active Compounds", 19990610, pp. 212-213.

(Continued)

*Primary Examiner* — Dennis Heyer
(74) *Attorney, Agent, or Firm* — Ping Wang; Andrews Kurth Kenyon LLP

(57) ABSTRACT

A method for treating and/or delaying the degeneration of Purkinje cells in a subject is provided. The method comprises administering to a subject in need thereof a therapeutically effective amount of a medicament, wherein the medicament comprises a phthalide selected from the group consisting of n-butylidenephthalide (BP), a metabolic precursor of BP, a pharmaceutically acceptable salt of a metabolic precursor of BP, a pharmaceutically acceptable ester of a metabolic precursor of BP, and combinations thereof.

9 Claims, 10 Drawing Sheets

(56) References Cited

OTHER PUBLICATIONS

Yu, Y. et al., "Protection against hydrogen peroxide-induced injury by Z-ligustilide in PC12 cells", Experimental Brain Research, 2008, vol. 184(3), pp. 307-312.
Paulson, H., "Machado-Joseph Disease/Spinocerebellar Ataxia Type 3", Handb Clin Neurol., 2012, vol. 103, pp. 437-449.

* cited by examiner

METHOD FOR TREATING AND/OR DELAYING THE DEGENERATION OF PURKINJE CELLS

FIELD

The present invention relates to the use of a phthalide, especially to the use of a phthalide in treating and/or delaying the degeneration of Purkinje cells. In particular, the present invention relates to the use of a phthalide in treating spinal cerebellar atrophy, Alzheimer's disease, and/or Parkinson's disease and/or delaying the onset thereof.

BACKGROUND

A neuron, also known as a nerve cell, is one of the structural and functional units of the nervous system of an organism. Neurons can transmit messages to other cells via chemical and electrical signals. Neurons can vary in shape and size, and the diameters of the neurons may range from about 4 μm to about 100 μm. The structure of a neuron can be roughly divided into three parts: a cell body, dendrites, and an axon, wherein the dendrites can transmit signals into the cell body, and the axon can transmit signals out from the cell body.

Purkinje cells belong to γ-aminobutyric acid (GABA) neurons in the cerebellum that are responsible for transmitting nerve impulses. Purkinje cells have a morphology larger than other neurons and have more dendrites. The main functions of Purkinje cells are transmitting neural signals and regulating sodium-potassium ion channels. Purkinje cells play a role in the coordination of movement in a living body. The degeneration of Purkinje cells (e.g., cell death, reduction in the number of cells, cellular damage, or a decrease in the signal transmission function caused by the reduction of dendrites) may damage the signal transmission function of Purkinje cells. It has been known that the degeneration of Purkinje cells is relevant to neuronal diseases, such as Alzheimer's disease, Parkinson's disease, and spinal cerebellar atrophy, and is a process indicator of these diseases (see Schilling, K. et al., 1991, Electrical activity in cerebellar cultures determines Purkinje cell dendritic growth patterns. Neuron 7, 891-902, which is entirely incorporated hereinto by reference). Accordingly, the treatment effects of the neuronal diseases, such as Alzheimer's disease, Parkinson's disease, and spinal cerebellar atrophy can be provided if the degeneration of Purkinje cells can be inhibited.

Spinocerebellar atrophy is one of the most common ataxia related disease. Patients of spinocerebellar atrophy commonly suffer from cerebellar ataxia, which results in movement coordination disorders, muscle tension reduction, eye movement disorders, and speech disorders, etc. Spinocerebellar atrophy is primarily caused by genetic or gene mutations, which leads to the production of abnormal CAG repeat sequences in the exon of Atxin-3 (ATXN3) gene on a specific chromosome and thus the long chain glutamine will be generated in the translated proteins and result in cell apoptosis. ATXN3 is a deubiquitinating enzyme (DUB). In the ubiquitin-proteasome pathway, ATXN3 plays a role in preventing abnormal protein aggregation. Depending on where the CAG repeat sequence is located in a patient, spinocerebellar atrophy can be classified into various subtypes, such as type 1 (SCA1), type 2 (SCA2), type 3 (SCA3), type 6 (SCA6), type 7 (SCAT), and DRPLA. SCA3, also known as Machado-Joseph disease (MJD), is the most common subtype of spinocerebellar atrophy, characterized by an abnormal CAG repeat sequence present in exon 10 of chromosome 14q32.1.

Currently, there are no effective treatments in the clinic for diseases caused by the degeneration of Purkinje cells. The patients can at best receive physical therapy and respiratory care to reduce the incidence of complications and slow the progression of the disease. Therefore, there is still a need for a medicament for treating and/or delaying diseases related to the degeneration of Purkinje cells.

The inventors of the present invention found that phthalide can treat and/or delay the degeneration of Purkinje cells, and thus, can be used to treat and/or delay the onset of spinocerebellar atrophy, Alzheimer's disease, and/or Parkinson's disease.

SUMMARY

An objective of the present invention is to provide the use of a phthalide in the manufacture of a medicament. The medicament is for treating and/or delaying the degeneration of Purkinje cells. The phthalide is selected from the group consisting of n-butylidenephthalide (BP), a metabolic precursor of BP, a pharmaceutically acceptable salt of a metabolic precursor of BP, a pharmaceutically acceptable ester of a metabolic precursor of BP, and combinations thereof.

Another objective of the present invention is to provide a method for treating and/or delaying the degeneration of Purkinje cells in a subject, comprising administering to a subject in need thereof a therapeutically effective amount of a medicament, wherein the medicament comprises a phthalide selected from the group consisting of BP, a metabolic precursor of BP, a pharmaceutically acceptable salt of a metabolic precursor of BP, a pharmaceutically acceptable ester of a metabolic precursor of BP, and combinations thereof.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIGS. 5A to 5C are curve diagrams showing the local motor tests results of SCA3 mice treated with different conditions, wherein FIG. 5A is a curve diagram showing the total moving distance of SCA3 mice treated with different conditions, FIG. 5B is a curve diagram showing the moving number of SCA3 ice treated with different conditions, and FIG. 5C is a curve diagram showing the moving time of SCA3 mice treated with different conditions;

DETAILED DESCRIPTION

Figure 1:
FIG. 1 is a fluorescent micrograph showing pEGFP-C1 transfected cells, pEGFP-C1-Ataxin3Q28 transfected cells, or pEGFP-C1-Ataxin3Q84 transfected cells treated with different conditions

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the" or the like recited in the specification of the present invention (especially in the claims) should include both the singular and plural forms. Furthermore, the term "an effective amount" used in this specification refers to the amount of the compound that can at least partially alleviate the condition that is being treated in a suspected subject when administered to the subject. The term "subject" used in this specification refers to a mammalian, including human and non-human animals. The term "treat" or "treating" includes the prevention of particular diseases and/or disorders, the amelioration of particular diseases and/or disorders, and/or the prevention or elimination of the diseases and/or disorder. The term "delaying the degeneration of Purkinje cells" refers to delaying cell death, damage, and/or reduction in message transmission functions. The unit "mg/kg-body weight" used in this specification means the dosage required per kg-body weight.

The inventors of the prevent invention found that certain phthalide can treat and/or delay the degeneration of Purkinje cells. Therefore, the present invention provides the use of a phthalide in the manufacture of a medicament for treating and/or delaying the degeneration of Purkinje cells, wherein the phthalide is selected from the group consisting of n-butylidenephthalide (BP), a metabolic precursor of BP, a pharmaceutically acceptable salt of a metabolic precursor of BP, a pharmaceutically acceptable ester of a metabolic precursor of BP, and combinations thereof.

According to one embodiment of the present invention, BP was used to prepare a medicament for treating and/or delaying the degeneration of Purkinje cells. BP has a formula of compound (I) as follows, which comprises two isomers in nature, i.e., Z-BP (cis-butylidenephthalide) and E-BP (trans-butylidenephthalide). Preferably, a BP that comprises 90% or more of Z-BP is used in the present invention.

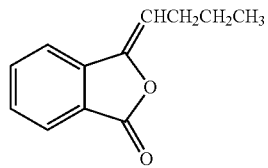

(I)

The term "metabolic precursor of BP" used in this specification refers to a compound whose metabolism in a living body will generate BP. Specific examples of a structural analogue of BP include, but are not limited to, 3-butylidene-4,5-dihydrophthalide (also known as ligustilide) as shown in following formula (II), which is a metabolic precursor of BP. That is, ligustilide will generate BP after being metabolized in a living body.

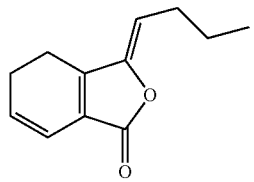

(II)

The term "pharmaceutically acceptable salt" used in this specification includes a pharmaceutically acceptable salt prepared from an acid group-containing phthalide and an organic or inorganic base. The salts prepared from inorganic bases, include but are not limited to alkali metal salts (e.g., sodium salts, potassium salts), alkaline earth metal salts (e.g., calcium salts, magnesium salts), transition metal salts (e.g., iron salts, zinc salts, copper salts, manganese salts, and aluminum salts), and ammonium salts. The salts prepared from organic bases, include but are not limited to the salts prepared from methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like.

The term "pharmaceutically acceptable ester" used in this specification includes an ester prepared from a hydroxyl-containing phthalide and an acid. The acid may be an inorganic acid such as hydrochloric acid, hydrobromic acid, sulfuric acid, sulfamic acid, nitric acid, and phosphoric acid, or an organic acid such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, 2-hydroxy ethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, and undecanoic acid.

The phthalide used in the present invention can be provided by any suitable manner. For example, ligustilide can be purified from angelica, xiong, and *Ligusticum sinense* Oliv., but not limited thereby. BP can be purified from angelica, or be purchased commercially. In addition, BP (i.e., a mixture of Z-BP and E-BP) purchased commercially can be embedded with a suitable amount of silicone (the weight ratio of BP:silicone=1:3), and then, analyzed by silica gel column chromatography, wherein the n-hexane may be used as a mobile phase elution solution. Z-BP and E-BP can be eluted and collected at different elution times.

As described above, the medicament provided by the present invention is effective in treating and/or delaying the degeneration of Purkinje cells, and especially can delay and/or prevent cell death of Purkinje cells and increase the ubiquitination of the proteins in Purkinje cells. Therefore, the medicament provided by the present invention can be used to treat and/or delay the onset of spinocerebellar atrophy, Alzheimer's disease, and/or Parkinson's disease. In some embodiments of the present invention, the medicament is used to treat and/or delay the onset of type 3 spinocerebellar atrophy (SCA3). As illustrated in the Examples provided in this specification, the medicament provided by the present invention can effectively delay and/or prevent the cell death of Purkinje cells in the cerebellum of patients suffering type 3 spinocerebellar atrophy and can effectively improve the motor behavior of the patients.

Depending on the requirements of the subject, the dosage of the medicament provided by the present invention can be adjusted. For example, when applied to the human body for treating and/or delaying the degeneration of Purkinje cells, the medicament is preferably administered at an amount ranging from about 30 mg (as the phthalide)/kg-body weight to about 2,000 mg (as the phthalide)/kg-body weight per day, and more preferably about 100 mg (as the phthalide)/kg-body weight to about 1,000 mg (as the phthalide)/kg-body weight per day. However, for patients with acute conditions, the dosage can be increased to several times or several tens of times, depending on the practical requirements. In addition, the total dosage can optionally be applied to a subject by a single administration process or multiple administration processes.

According to the present invention, the medicament can be in any suitable dosage form for administration, and be applied in any suitable way. For example, the medicament can be manufactured into a dosage form that is suitable for oral administration, nasal administration, intravenous injection, intraperitoneal injection, subcutaneous injection, and/or be manufactured into a controlled release dosage form for subcutaneous or inter-tissue administration. Because a medicament in an oral administration form is convenient for self-administration, in one preferred embodiment of the present invention, the medicament is provided in an oral administration form such as a tablet, a capsule, a granule, powder, a fluid extract, a solution, syrup, a suspension, an emulsion, a tincture, etc. Depending on the dosage form and purpose, the medicament can further comprise a pharmaceutically acceptable carrier. In some embodiments of the present invention, olive oil was used as a carrier.

Using the manufacturing of a medicament suitable for oral administration as an example, the medicament may comprise a pharmaceutically acceptable carrier which has no adverse effect on the desired activity of the active component (i.e., BP, a metabolic precursor of BP, and/or a pharmaceutically acceptable salt and/or ester of a metabolic precursor of BP), such as an oily solvent, diluent, stabilizer, absorption delaying agent, disintegrant, emulsifier, antioxidant, binder, lubricants, and moisture absorbent. The medicament can be prepared into an oral administration dosage form by any suitable methods.

For medicaments suitable for subcutaneous injection or intravenous injection, the medicament may comprise one or more components such as an isotonic solution, a saline buffer solution (e.g., a phosphate buffer or a citric acid salt buffer), a solubilizer, an emulsifier, and other carriers to manufacture the medicament as an intravenous injection, an emulsion intravenous injection, a powder injection, a suspension injection, or a powder-suspension injection.

In addition to the above adjuvants, the medicament may optionally comprise other additives, such as a flavoring agent, a toner, a coloring agent, etc. to enhance the taste and visual appeal of the resultant medicament. To improve the storability of the resultant medicament, the medicament may also comprise a suitable amount of a preservative, a conservative, an antiseptic, an anti-fungus reagent, etc. Furthermore, the medicament according to the present invention may optionally comprise one or more other active components, such as an antioxidant (e.g., vitamin E), neurotrophic factors, etc., to further enhance the efficacy of the medicament or to increase the application flexibility and adaptability of the medicament, as long as the other active components have no adverse effect on the phthalide contained in the medicament.

In addition, depending on the requirements of a subject, the medicament according to the present invention can be applied to the subject with various administration frequencies, such as once a day, several times a day, or once for several days, etc.

The present invention also provides a method for treating and/or delaying the degeneration of Purkinje cells in a subject, comprising administering to a subject in need thereof a therapeutically effective amount of a phthalide selected from the group consisting of BP, a metabolic precursor of BP, a pharmaceutically acceptable salt of a metabolic precursor of BP, a pharmaceutically acceptable ester of a metabolic precursor of BP, and combinations thereof. The selection, property, administration, and dosage of the phthalide are all as described hereinabove.

The present invention will be further illustrated in detail with specific examples as follows. However, the following examples are provided only for illustrating the present invention, and the scope of the present invention is not limited thereby.

EXAMPLES

[Example 1] In Vitro Cell Test

Cell Transfection

In this experiment, the effects of BP and ligustilide on the protein expression level of SCA3 protein were analyzed. First, pEGFP-C1-Ataxin3Q84 plasmid (i.e., a plasmid comprising Ataxin gene with abnormal CAG repeat number (84Q)) containing green fluorescent protein or pEGFP-C1-Ataxin3Q28 plasmid (i.e., a plasmid comprising Ataxin gene with normal CAG repeat number (28Q)) (Addgene company, U.S.) was transfected into human embryonic kidney (HEK) cells 293T (Bioresource Collection and Research Center, Taiwan) or neural stem cells (NSC). The cells were then cultured in a DMEM medium (Dulbecco's modified Eagle's medium, Thermo) containing 10% fetal bovine serum (Gibco), and incubated in an incubator with 5% $CO_2$ at 37° C. Then, the cells were treated with 5 μg/ml BP (A10353, purchased from Alfa Aesar, U.S.; with a purity of 95%) or ligustilide (5393-015M1, purchased from Pharmaron, China) for 24 hours. The protein aggregation of GFP-ATXN3 protein in the cells of each group was observed by a fluorescence microscopy. Wild type cells and cells transfected with green fluorescent protein (GFP) were used as the control group. The experimental results are shown in FIG. 1.

As shown in FIG. 1 (the scale in the lower right corner is 100 μm), the cells that were not transfected with GFP showed no fluorescence, while the cells transfected with the plasmid showed significant fluorescence, revealing that the cells can successfully express GFP and ATXN3. In addition, the fluorescent signal of Ataxin3Q84 shown in the cells treated with BP or ligustilide was significantly lower than that of the untreated groups, revealing that BP and ligustilide can reduce the expression of ATXN3 protein.

[Example 2] In Vivo Zebrafish Test (1) Safe Dose Test

In this experiment, the zebrafishes that were used as the animal models in the experimental group were Tg (HuC: GFP), which is characterized by its primary sensory neurons (Rohon-Beard cells) that can produce fluorescence. The zebrafishes used in the control group were wild type zebrafishes. All of the zebrafishes were provided by TZCAS (Taiwan Zebrafish Core Facility at Academia Sinica, Taiwan) and TZCF (Taiwan Zebrafish Core Facility, Taiwan). First, the toxicity of BP to zebrafish was tested by injecting different dose of BP to zebrafishes. The zebrafishes were then kept at 28.5° C. After 48 hours, the survival rate of the zebrafishes was observed.

Figure 2:
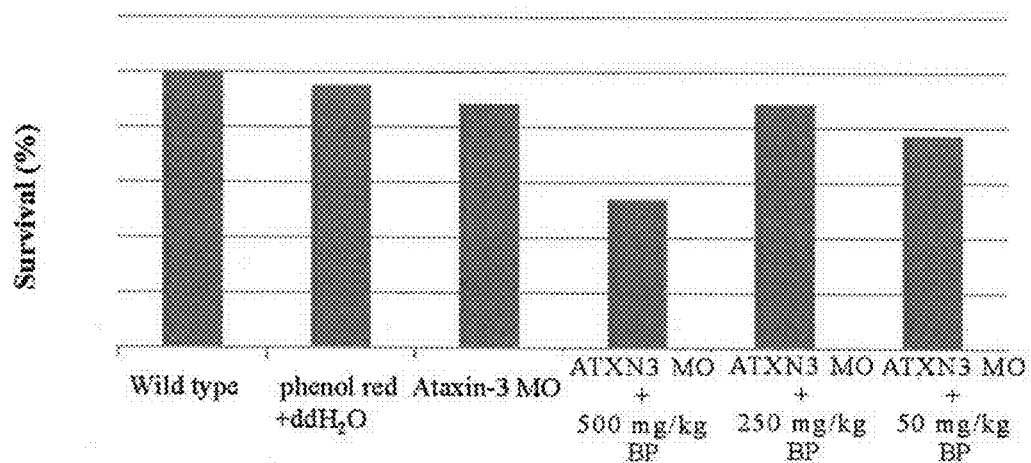
FIG. 2 is a bar diagram showing the survival rate of zebra fish treated with different conditions.

As shown in FIG. 2, the survival rate of the wild type zebrafishes was 100%. The survival rate of the zebrafishes treated with 500 mg/kg BP was 50%, and both of the survival rates of the zebrafishes treated with 250 mg/kg and 50 mg/kg BP were greater than 75%. The survival rate of the zebrafishes injected with ATXN3 MO or $H_2O$ was slightly reduced, which may be due to infection caused by injection or poor egg quality. These data showed that a dose of BP lower than 250 mg/kg was a safe dose for zebrafish.

(2) Behavioral Test

In this experiment, the morpholinos DNA fragment of the ATXN3 gene (Gene Tools, U.S; hereinafter referred to as "ATXN3 MO") was used to deactivate the expression of endogenous ATXN3 in zebrafish, and thereby, resulted in an effect of neurological damage.

Morpholinos (MO) was produced by modifying the structure of a fragment of DNA, which can block protein translation process of mRNA to inhibit the expression of a target protein. The ATXN3 MO used in this experiment has a sequence of 5'-TCCTCCTCGTCCAGCTGCTGTGCTA-3' (SEQ ID NO. 1), and the standard used in the control group is 5'-CCTCTTACCTCAGTTACAATTTATA-3' (SEQ ID NO. 2) (hereinafter referred to as "Ct MO"). Before injection, the MO was dissolved in $ddH_2O$, stored at −20° C. for used. Zebrafish eggs were micro-injected within about one hour after birth. After 21 to 48 hours post fertilization (hpf), the zebrafish eggs were micro-injected with ATXN3 MO or ATXN3 MO in combination with 250 mg/kg BP, 125 mg/kg BP or 62.5 mg/kg BP. After 48 hours, the fish tails were stimulated by tips, and the number of stimulation causing movement of the fish tails was measured.

Figure 3:
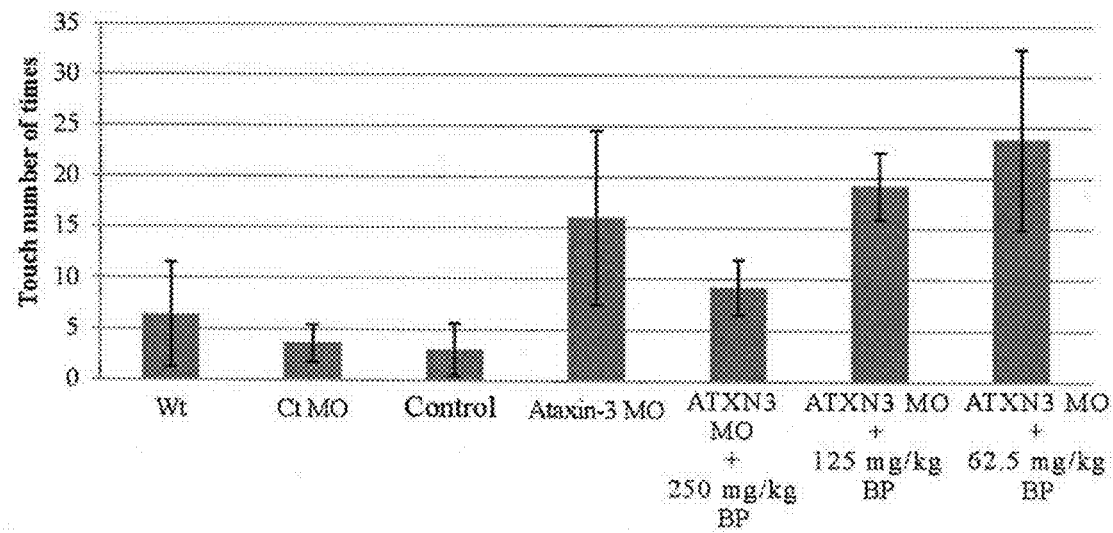
FIG. 3 is a bar diagram showing the behavioral tests results of zebra fish treated with different conditions.

As shown in FIG. 3, as compared to the wild type group (hereinafter referred to as "Wt") and control group (hereinafter referred to as "Mock"), the amount of stimulation causing the movement of fish tails was significant higher in the zebrafishes injected with ATXN3 MO. The amount of stimulation causing the movement of fish tails was restored (i.e., decreased) in the zebrafishes treated with BP. These results showed that BP can restore the behavioral ability of the diseased zebrafishes, wherein BP of 250 mg/kg concentration showed the most obvious effect.

(3) Confocal Microscopy Test

Zebrafish eggs were micro-injected with 300 nM/μl ATXN3 MO, 250 mg/kgBP, or ATXN3 MO in combination with 250 mg/kgBP, 125 mg/kg BP or 62.5 mg/kgBP. After 48 hours, the zebrafishes were enclosed in glass slides. The motor neurons in the living body were recorded by a confocal fluorescence microscopy.

Figure 4:
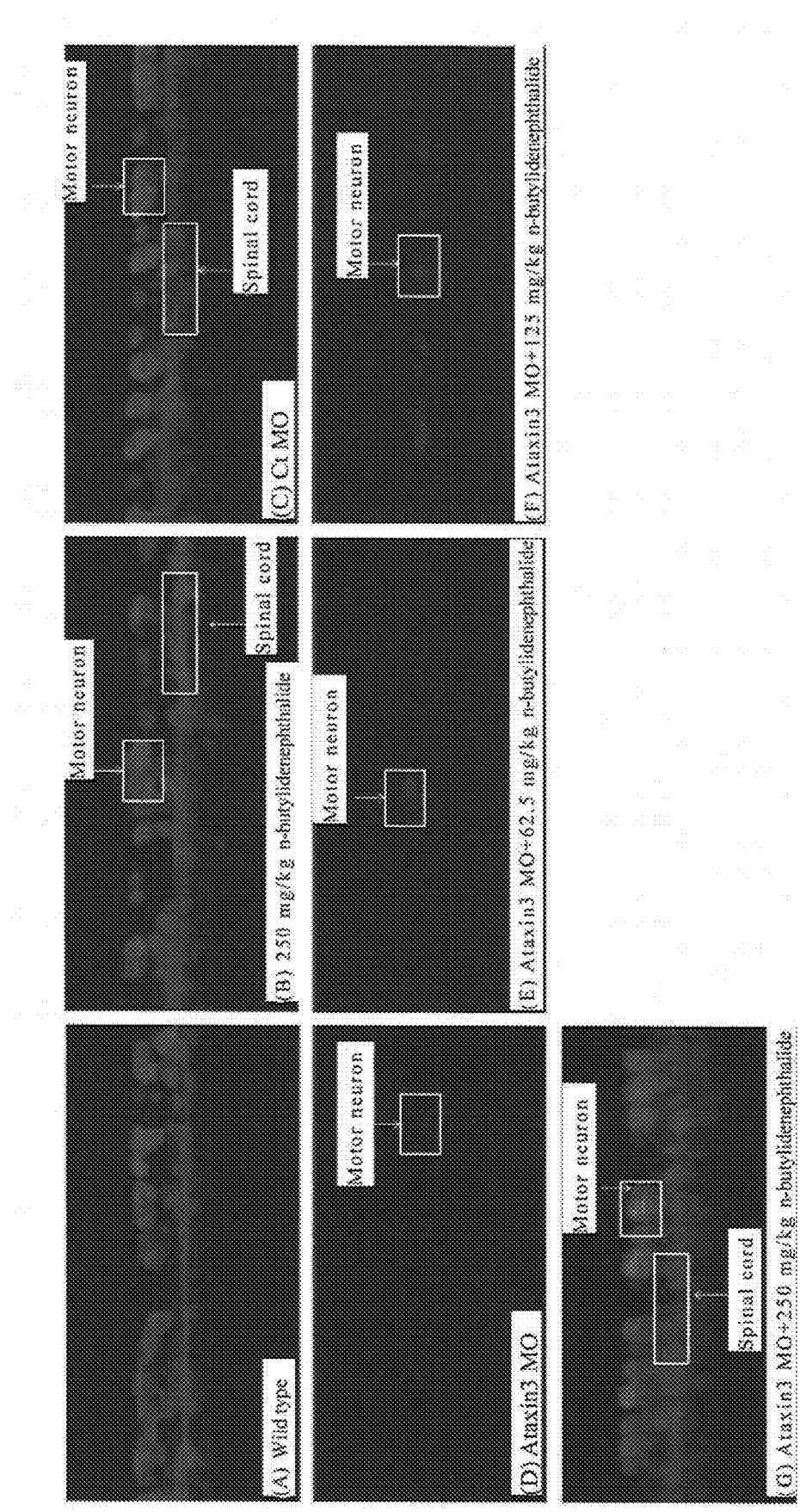
FIG. 4 is a confocal micrographs showing the neurons of zebra fish treated with different conditions.

The experimental results showed that the neuron of the wild type zebrafishes showed no neurological damage, while the zebrafishes only treated with Ct MO also showed no significant neurological damage. After the zebrafishes were injected with Ataxin-3 MO, the neurological signals in the zebrafishes were significantly decreased. This shows that Ataxin-3 MO can cause neurological damage and has specificity. In addition, as shown in FIG. 4, the treatment of 250 mg/kg BP to the zebrafishes treated with ATXN3 MO can maintain the number of motor neurons. The data shown in FIG. 4 was obtained by 100%*(the number of the survived zebrafishes/total number of the zebrafishes).

[Example 3] In Vivo Mice Test

MJD84.2 transgenic mice (i.e., the mice being transfected with ATXN3 gene with human 84 CAG repeat sequence, hereinafter referred to as "SCA3 mice") were used in this experiment. MJD84.2 transgenic mice were an animal model used for studying spinal cerebellar atrophy. These mice will show abnormal gait four weeks after birth, and then will gradually show mild tremor, moderately decreased activity, abnormal contraction of front/hind limbs (at about 24 weeks of age), and inability to lie to the ground.

(1) Treatment of MJD84.2 Transgenic Mice

The MJD84.2 transgenic mice of two weeks of age were randomly divided into five groups, each group had six mice. The mice were treated with the following conditions for two weeks: (1) untreated group; (2) treated with olive oil (i.e., only treated with the adjuvant); (3) treated with 100 mg/kg/bid (bis in die) of BP; (4) treated with 500 mg/kg/bid of BP; (5) treated with 100 mg/kg/bid of ligustilide. The wild type mice (WT) was used as a control group. After 2 weeks, local motor and rotarod test were conducted.

(2) Local Motor Test

Local motor test was performed to test the exercise ability of mice. 10-week-old mice were tested on rotarod once every three weeks. Then, the mice were placed in a transparent acrylic box 2 hours and were free to move. A behavioral test was conducted for 1 hour by using VersaMax 420 (AccuscanInstrumentsInc, USA), and the data was analyzed by statistical methods.

Figure 5:
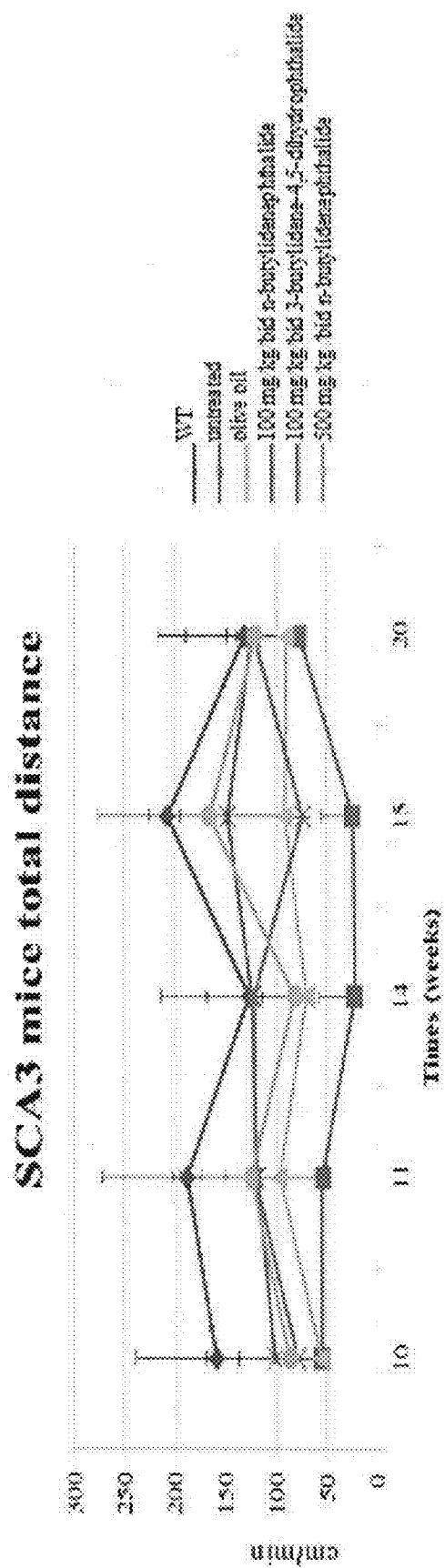
Figure 5B:
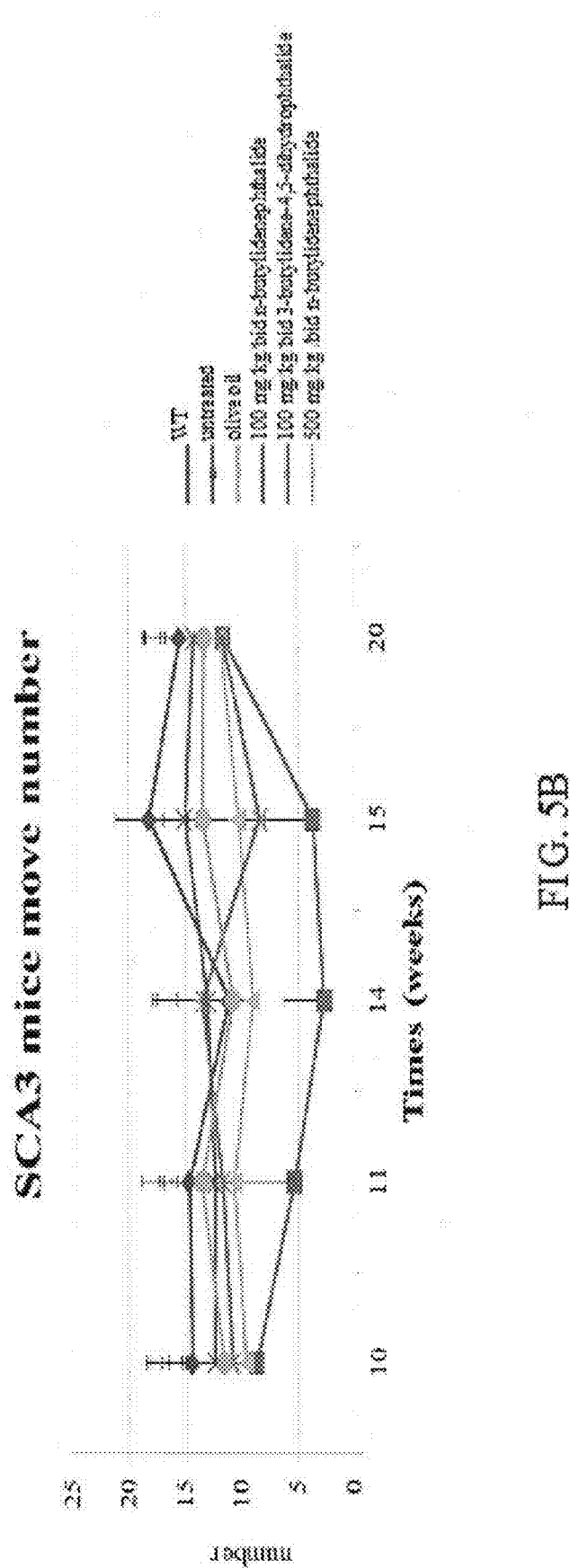
Figure 5C:
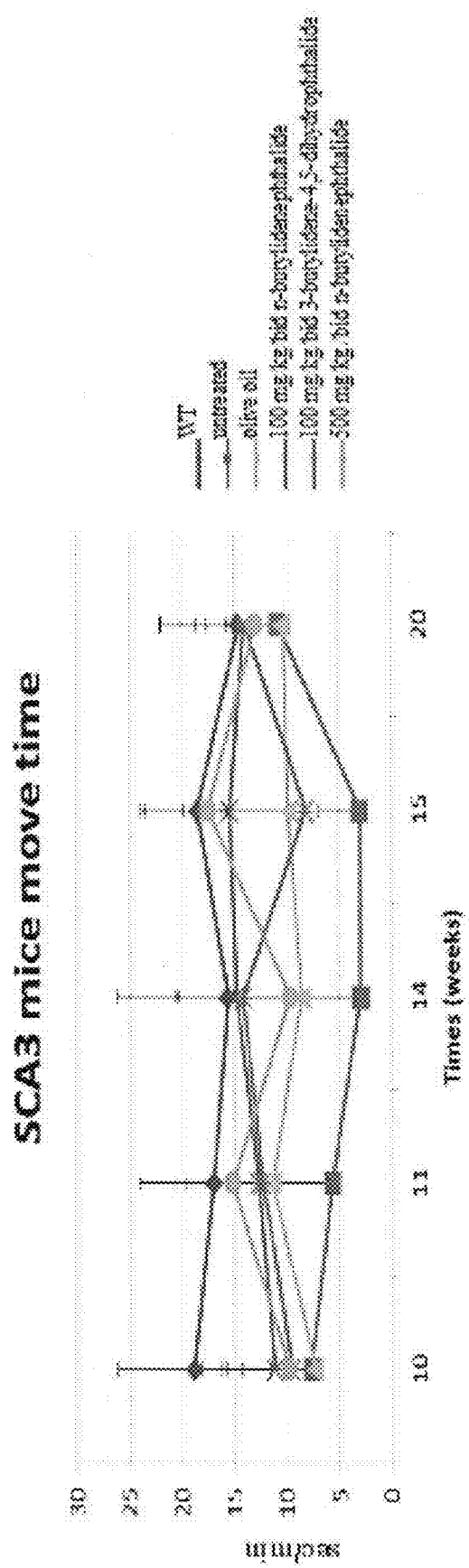

The results are shown in FIGS. 5A, 5B, and 5C. As compared to the untreated group and the group fed with olive oil, the total moving distance (FIG. 5A), moving times (FIG. 5B) and moving time (FIG. 5C) of the mice treated with BP or ligustilide were higher, revealing that the mice treated with BP or ligustilide had a better exercise ability. These data show that BP and ligustilide can improve the exercise behavior of the MJD84.2 transgenic mice.

(3) Rotarod Test

Rotarod test was performed to test the balance and grip ability of mice. The mice were given practice two weeks before the first behavioral test. The experiment was conducted using an IITC rotarod (IITC Life Science Inc, USA).

10-week-old mice were tested on a rotarod once every three weeks. The test condition was set as a linear acceleration from 4 to 40 rpm within 300 seconds. The time (sec) that the mice fell from the rotarod (i.e., latency to fall) was recorded. Each test was continued for at most 5 minutes, and the mice were at rest for at least 15 minutes between each test to avoid fatigue. After the rotarod test, the body weight of the mice were recorded. The test was conducted three times a day for four consecutive days, and the statistical analysis was performed using the daily average time before the mice fell from the rotarod.

Figure 6:
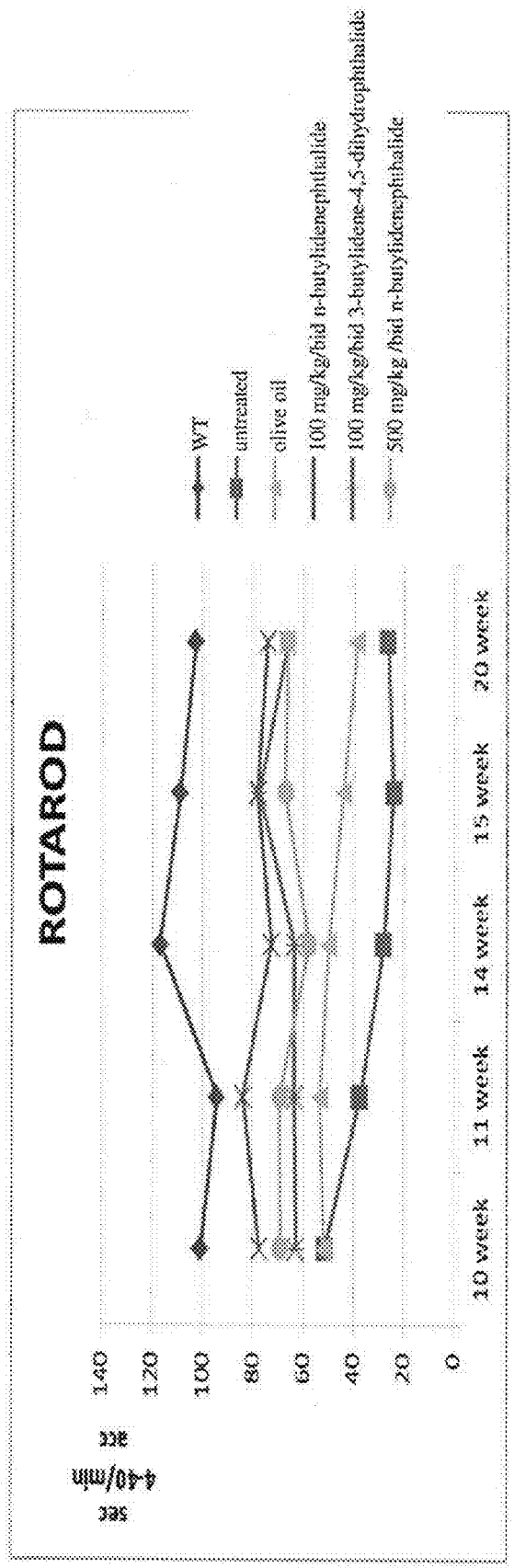
FIG. 6 is a curve diagram showing the rotarod tests results of SCA3 mice treated with different conditions.

As shown in FIG. 6, as compared to the untreated group and the group fed with olive oil, the balance and grip ability of the mice treated with BP or ligustilide were better, revealing that BP and ligustilide can improve the exercise behavior of the MJD84.2 transgenic mice.

[Example 4] Immunohistochemistry Staining Assay

The MJD84.2 transgenic mice (i.e., the mice with modified ATXN3 gene) of eight weeks of age were randomly divided into five groups, with six mice in each group. The mice were treated with the following conditions: (1) untreated group; (2) treated with olive oil; (3) treated with 100 mg/kg/bid of BP; (4) treated with 500 mg/kg/bid of BP; (5) treated with 100 mg/kg/bid of ligustilide. Then, the mice were sacrificed at the age of 20 weeks and 24 weeks. Cerebellar slices staining and tissue protein extraction were performed (see Example 5). Whole brain tissue of the mice was fixed overnight with 3.7% formalin and embedded in paraffin. The samples were sectioned (4 μm) by using a Quanto kit (Thermo, USA) and mounted on a microscope slide.

Figure 7:
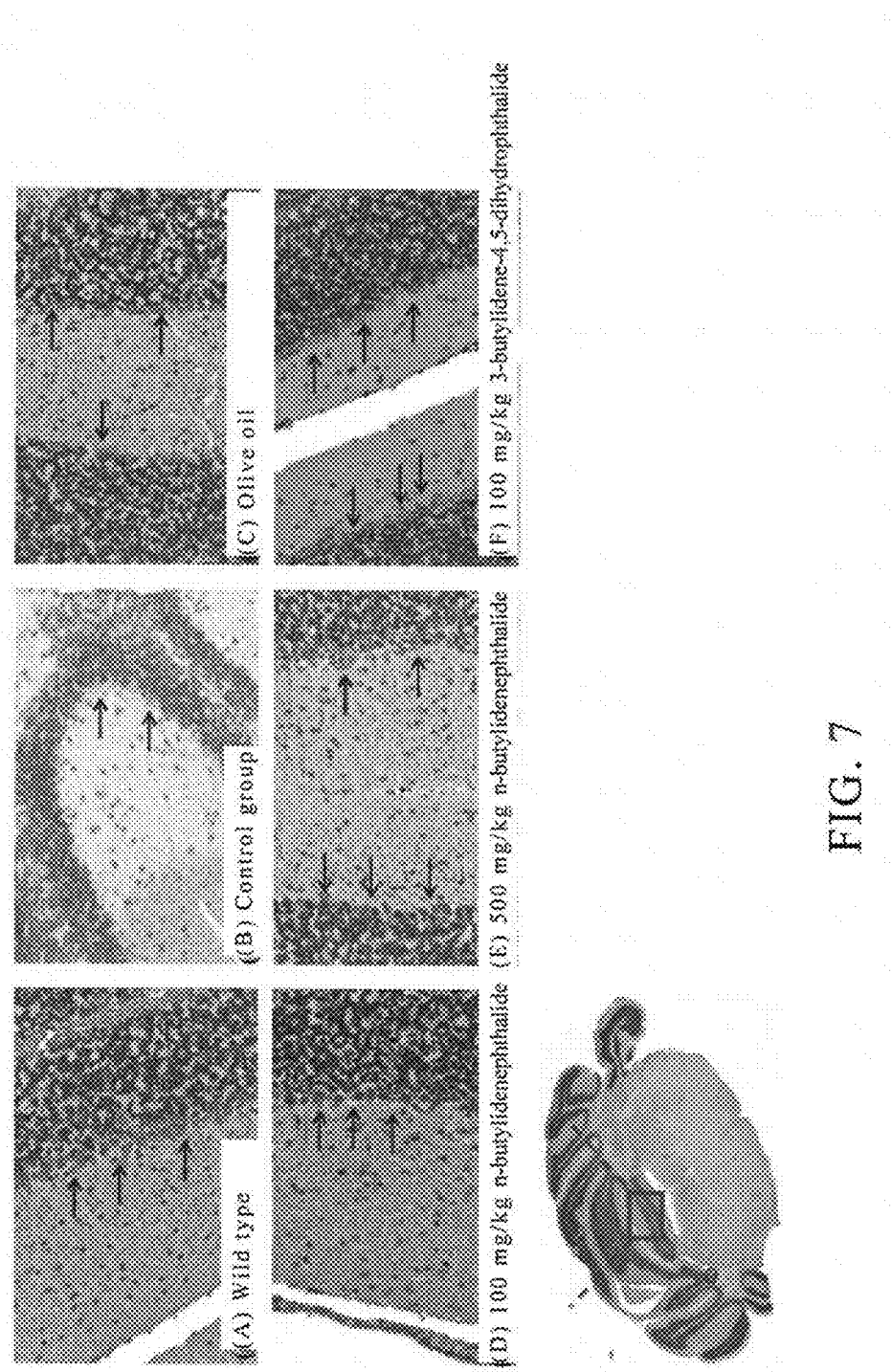
FIG. 7 is an immunochemical staining picture showing the cerebellar slices of SCA3 mice treated with different conditions.

FIG. 7 showed the immunohistochemistry staining results of the slice of the cerebellum in the SCA3 mice. The Purkinje cells of the mice in the untreated group and the group fed with olive oil showed significant deficiency, while the number of the Purkinje cells of the mice in the group treated with BP or ligustilide was significantly higher than that of the untreated group and the group fed with olive oil. These data show that BP and ligustilide can delay and/or prevent the death of Purkinje cells.

ubiquitin and calbindin in the cerebellum tissue of SCA3 mice in each group. β-actin was used as an internal control group.

Figure 8:
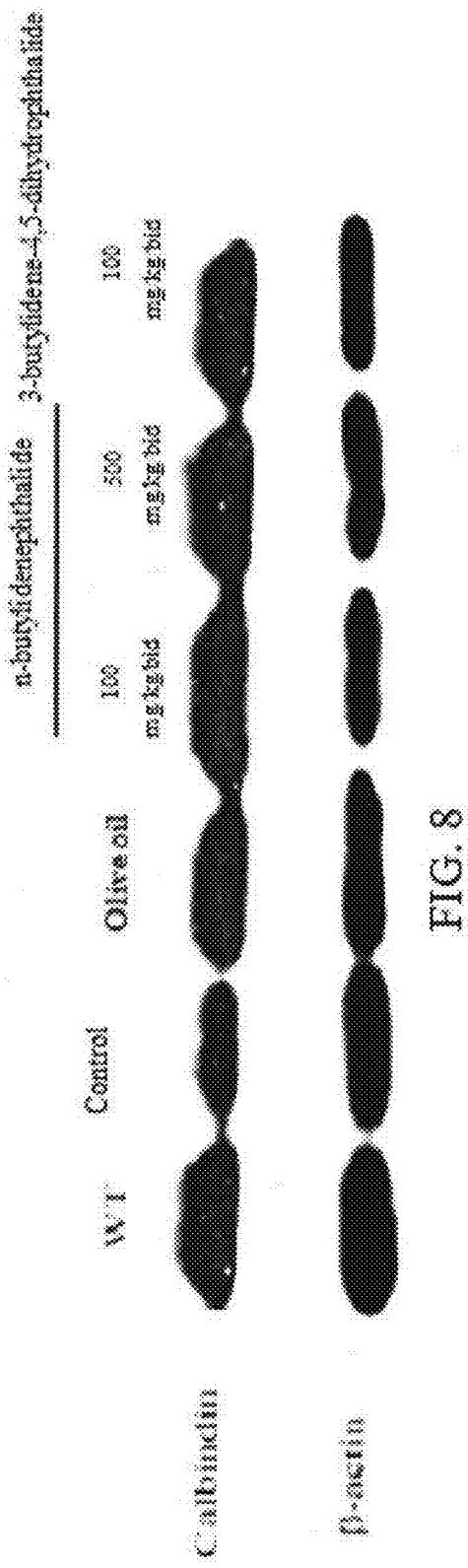
FIG. 8 is a Western blot picture showing the calcium-binding protein in the cerebellum tissue of SCA3 mice treated with different conditions.

As shown in FIG. 8, as compared to the untreated group and the group fed with olive oil, the protein expression level of calbindin of the mice treated with BP or ligustilide were significantly higher. It has been known that calbindin is a marker of Purkinje cells. The experimental results of this example and the slices both showed the increase of the number of Purkinje cells, revealing that BP and ligustilide can slow the disease progression of SCA3.

Figure 9:
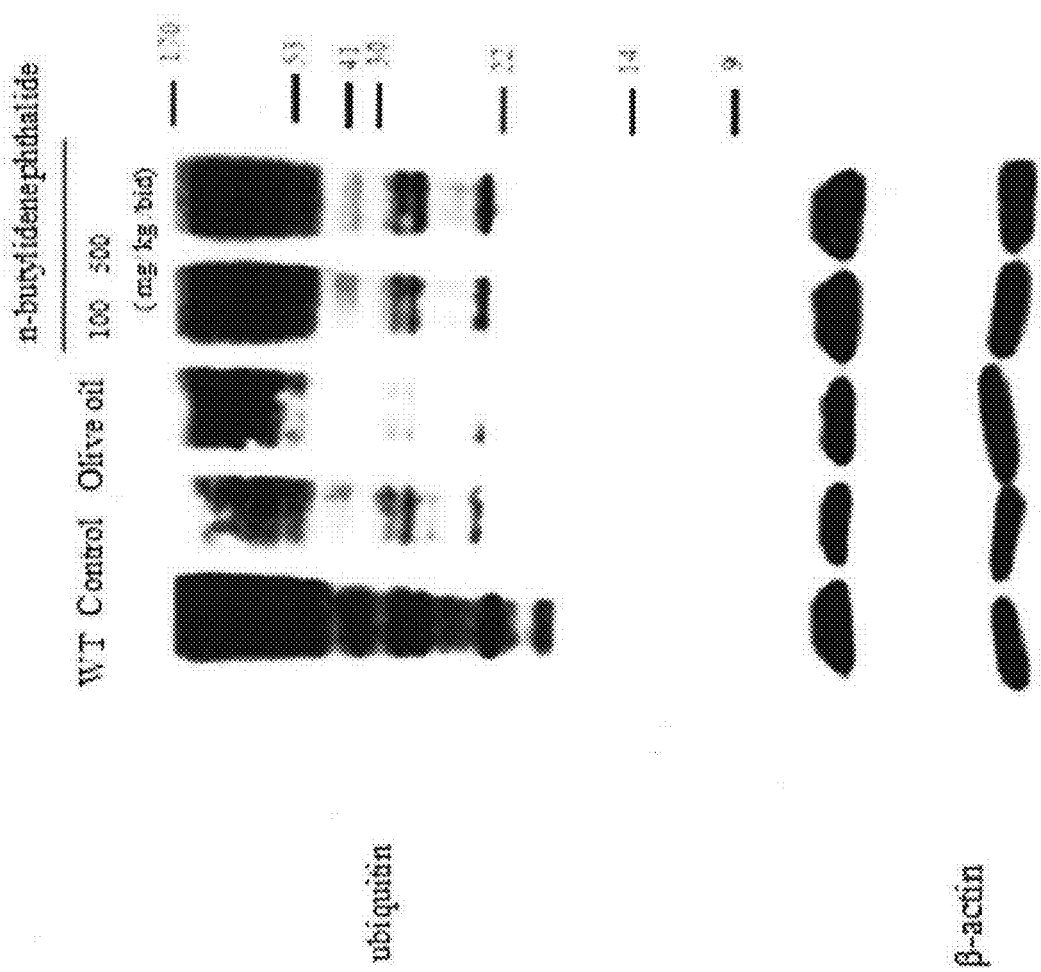
FIG. 9 is a Western blot picture showing the ubiquitinated proteins in the cerebellum tissue of SCA3 mice treated with different conditions.

In addition, as shown in FIG. 9, as compared to the untreated group and the group fed with olive oil, the content of the ubiquitin ubiquitination proteins of the mice treated with BP was significantly higher, revealing that BP is effective in increasing the ubiquitination conducted by ubiquitin. That is, BP can increase the ubiquitination of the proteins in cerebellum neurons, and thereby, can increase the efficiency of proteasome to metabolize abnormal proteins to slow the disease progression of SCA3.\

The results of the above examples show that the phthalide involved in the present invention can treat and/or delay the degeneration of Purkinje cells, and thus, can be used to treat and/or delay the onset of spinal cerebellar atrophy, Alzheimer's disease, and/or Parkinson's disease.

The above examples are used to illustrate the principle and efficacy of the present invention but not used to limit the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: ATXN3 MO

<400> SEQUENCE: 1
tcctcctcgt ccagctgctg tgcta                                           25

<210> SEQ ID NO 2
<211> LENGTH: 25
<212> TYPE: DNA
<213> ORGANISM: Artificial Sequence
<220> FEATURE:
<223> OTHER INFORMATION: Control MO

<400> SEQUENCE: 2
cctcttacct cagttacaat ttata                                           25
```

[Example 5] Western Blotting Assay

The cerebellums of the mice sacrificed in example 4 were separated from the whole brain, and the proteins in the cerebellums were extracted. The purified proteins were analyzed by Western blotting assay using an anti-ubiquitin antibody and an anti-calbindin antibody, respectively, to determine the changes in the protein expression level of

What is claimed is:

1. A method for delaying the onset of spinal cerebellar atrophy in a subject having abnormal CAG repeat sequences in the exon of ATXN3, comprising administering to the subject a therapeutically effective amount of a medicament, wherein the medicament comprises a phthalide selected from the group consisting of n-butylidenephthalide (BP), a metabolic precursor of BP, and combinations thereof, wherein the metabolic precursor of BP is 3-butylidene-4,5-dihydrophthalide (ligustilide).

2. The method of claim 1, wherein the phthalide is BP.

3. The method of claim 2, wherein the BP comprises at least about 90% of Z-BP.

4. The method of claim 1, wherein the phthalide is 3-butylidene-4,5-dihydrophthalide (ligustilide).

5. The method of claim 1, wherein the medicament comprises olive oil as a carrier.

6. The method of claim 1, wherein the medicament is in a dosage form for oral administration, nasal administration, or intravenous injection, or in a controlled release dosage form for subcutaneous or inter-tissue administration.

7. The method of claim 1 for delaying the onset of spinal cerebellar atrophy type 3.

8. The method of claim 1, wherein the medicament is administered at an amount ranging from about 30 mg (as BP)/kg-body weight to about 2,000 mg (as BP)/kg-body weight per day.

9. The method of claim 8, wherein the medicament is administered at an amount ranging from about 100 mg (as BP)/kg-body weight to about 1,000 mg (as BP)/kg-body weight per day.

* * * * *